(12) United States Patent
Albert et al.

(10) Patent No.: US 8,905,049 B2
(45) Date of Patent: Dec. 9, 2014

(54) PROCESS FOR TREATING KERATIN FIBRES USING A NON-DETERGENT COSMETIC COMPOSITION COMPRISING AT LEAST ONE CALCIUM SALT

(75) Inventors: Anne-Sophie Albert, Paris (FR); Samira Khenniche, Clichy (FR); Isabelle Rollat-Corvol, Paris (FR)

(73) Assignee: L'Oreal, Paris (FR)

(*) Notice: Subject to any disclaimer, the term of this patent is extended or adjusted under 35 U.S.C. 154(b) by 0 days.

(21) Appl. No.: 13/821,994

(22) PCT Filed: Sep. 23, 2011

(86) PCT No.: PCT/EP2011/066600
§ 371 (c)(1),
(2), (4) Date: Aug. 15, 2013

(87) PCT Pub. No.: WO2012/038535
PCT Pub. Date: Mar. 29, 2012

(65) Prior Publication Data
US 2013/0319447 A1      Dec. 5, 2013

Related U.S. Application Data

(60) Provisional application No. 61/389,914, filed on Oct. 5, 2010.

(30) Foreign Application Priority Data

Sep. 24, 2010   (FR) ...................................... 10 57711

(51) Int. Cl.
*A61Q 5/00*   (2006.01)
*A61Q 5/12*   (2006.01)
*A61K 8/20*   (2006.01)
*A61K 8/19*   (2006.01)
*A61Q 5/02*   (2006.01)

(52) U.S. Cl.
CPC ... *A61K 8/19* (2013.01); *A61Q 5/12* (2013.01); *A61K 8/20* (2013.01); *A61Q 5/02* (2013.01)
USPC ......... 132/202; 424/70.1; 424/70.2; 424/70.4

(58) Field of Classification Search
USPC .................. 132/202; 424/70.1, 70.2, 70.4
See application file for complete search history.

(56) References Cited

U.S. PATENT DOCUMENTS

| | | | |
|---|---|---|---|
| 3,971,391 A | 7/1976 | Bore et al. | |
| 4,137,180 A | 1/1979 | Naik et al. | |
| 4,185,087 A | 1/1980 | Morlino | |
| 4,841,997 A | 6/1989 | Petrow | |
| 4,874,554 A | 10/1989 | Lange et al. | |
| 4,957,732 A | 9/1990 | Grollier et al. | |
| 5,472,697 A * | 12/1995 | Hirano et al. | .................. 424/401 |
| 5,565,192 A | 10/1996 | Leroy et al. | |

FOREIGN PATENT DOCUMENTS

| | | |
|---|---|---|
| DE | 92 10 516 | 1/1994 |
| EP | 0 186 507 A2 | 7/1986 |
| EP | 0 225 261 A1 | 6/1987 |
| EP | 0 342 834 A2 | 11/1989 |
| EP | 0 530 974 A1 | 3/1993 |
| EP | 0 626 166 A1 | 11/1994 |
| EP | 2 098 218 A1 | 9/2009 |
| EP | 2 196 178 A1 | 6/2010 |
| EP | 2 272 489 A1 | 1/2011 |
| FR | 2 589 476 A1 | 5/1987 |
| JP | 7002627 A | 1/1995 |
| JP | 2000191514 A | 7/2000 |
| JP | 2002047119 A | 2/2002 |
| JP | 2003095891 A | 4/2003 |
| WO | 95/01152 A1 | 1/1995 |
| WO | 2006/011771 A1 | 2/2006 |

OTHER PUBLICATIONS

International Search Report for PCT/EP2011/066600, (2011).
PCT/IB/308 Form for PCT/EP2011/066600, (2011).
English language Abstract for EP 0 225 261 (believed to be related to FR2589476), (1987).
English language Abstract for JP 7002627, (1995).
English language Abstract for JP 2000191514, (2000).
English language Abstract for JP 2002047119, (2002).
English language Abstract for JP 2003095891, (2003).
Todd & Byers, "Volatile Silicone Fluids for Cosmetics," Cosmetics and Toiletries, vol. 91, Jan. 1976, pp. 27-32.
Porter, M.R., Handbook of Surfactants, published by Blackie & Son (Glasgow and London), 1991, pp. 116-178.

* cited by examiner

*Primary Examiner* — Eisa Elhilo
(74) *Attorney, Agent, or Firm* — The Marbury Law Group, PLLC

(57) ABSTRACT

The present invention relates to a cosmetic process for treating keratin fibers, in particular human keratin fibers such as the hair, comprising a step in which a non-detergent cosmetic composition comprising, in a cosmetically acceptable medium, an amount of greater than or equal to 1% by weight, relative to the total weight of the composition, of one or more water-soluble inorganic calcium salts, is applied to the said keratin fibers, and a step of rinsing the said keratin fibers.

19 Claims, No Drawings

PROCESS FOR TREATING KERATIN FIBRES USING A NON-DETERGENT COSMETIC COMPOSITION COMPRISING AT LEAST ONE CALCIUM SALT

This is a national stage application of PCT/EP2011/066600, filed internationally on Sep. 23, 2011, which claims priority to U.S. Provisional Application No. 61/389,914, filed on Oct. 5, 2010, as well as French Application FR 1057711, filed on Sep. 24, 2010.

The present invention relates to a process for treating keratin fibres, in particular human keratin fibres such as the hair, comprising a step of applying a non-detergent cosmetic composition comprising an amount of greater than or equal to 1% by weight, relative to the total weight of the composition, of one or more water-soluble inorganic calcium salts and a step of rinsing the said keratin fibres. In particular, the invention relates to a process for conditioning keratin fibres, especially human keratin fibres such as the hair.

Many people are unsatisfied with the way their hair looks, and have difficulty in styling it. Hair is generally subject to the action of external atmospheric agents, such as light and bad weather. Furthermore, mechanical treatments such as brushing, combing or plaiting, or long-lasting dyeing, colouring, permanent-waving, thiol- or alkali-mediated straightening or alkali-mediated relaxing cosmetic treatments also damage and embrittle the hair.

These mechanical or chemical attacking factors thus make the hair dry, coarse, dull and brittle especially in the fragile places, and more particularly at the ends. Moreover, substantial hygrometry also usually leads to swelling of the head of hair, which makes it increasingly difficult to manage.

To overcome this, products for improving the appearance of the hair have been developed. These products are generally cosmetic compositions such as shampoos or hair conditioners, leave-in products, masks or sera.

Thus, international patent application WO 95/01152 describes compositions comprising cationic conditioning agents that may be combined with silicone conditioning agents. These products have satisfactory cleansing effects, but form a structure around the hair that is not always uniform.

One drawback associated with the use of these haircare compositions lies in the fact that silicones make the hair very heavy and lank, this phenomenon being known as "build-up". Thus, these compositions leave the hair lank, not fine over the entire length, and slow to dry. Even after drying and styling, the hair does not have all the desired softness, sheen and lightness. The haircare potential of compositions containing such silicones is thus limited.

In the field of cosmetic care, it is also known practice to use cleansing compositions comprising ions, as in Japanese patent JP 2002047119 or in Japanese patent application JP 2000191514.

Japanese patent application JP 2003095891 proposes, for its part, compositions comprising salts of quaternary ammonium type that are easy to rinse out.

However, such cosmetic compositions cannot afford satisfactory cosmetic properties as well as good control of the head of hair and of its volume.

There is thus a real need to develop a process for obtaining good cosmetic properties, whilst simultaneously improving the hairstyle hold properties and controlling the volume of the head of hair irrespective of the relative humidity of the air and of the hair type.

Thus, the aim of the present invention is to develop a process for achieving these objectives.

Surprisingly and advantageously, the Applicant has just discovered that the use of a cosmetic process for treating keratin fibres, comprising the application, to the said fibres, of a non-detergent cosmetic composition comprising one or more water-soluble inorganic calcium salts in an amount of greater than or equal to 1% by weight, relative to the total weight of the composition, and rinsing of the said fibres, makes it possible to solve the problems mentioned above.

Specifically, it has been found that the process according to the invention can give keratin fibres, and more particularly the hair, improved cosmetic properties especially as regards the sheen, the smoothness, the suppleness, the lightness, the uniformity and the fineness (sensation of having finer hair), while at the same time controlling the volume of the hair.

The term "non-detergent cosmetic composition" means a cosmetic composition comprising less than 4% by weight of anionic, amphoteric or nonionic surfactants relative to the weight of the composition.

In particular, on wet hair, smoother, more supple, finer hair is obtained. The drying time is markedly reduced. In addition, once dried, the hair is also smoother, shinier, finer and lighter, and has a more silky feel.

Moreover, the process according to the invention enables control of the head of hair and of its volume at various relative humidities, especially at relative humidities that may range from 20% to 80%. The hairstyle thus remains in place more easily, and for longer, the volume of the head of hair is controlled, and the frizzing is greatly reduced. The process according to the invention makes it possible, for example, to control the volume of the head of hair in a humid climate on natural to sensitized hair, which may be frizzy, over a period of more than 24 hours, while at the same time maintaining a natural appearance and a satisfactory feel.

The relative humidity (RH) or hygrometry represents the measurement of the amount of water in the air. This measurement is taken using a machine such as a psychrometer or a capacitive-probe hygrometer, and is defined by the ratio of the pressure exerted by the water vapour contained in the air at a given temperature to the saturating vapour pressure (i.e. the maximum amount of water vapour that this air could absorb at this temperature). It is given as a percentage on a scale ranging from 0 to 100%.

Furthermore, it has been found that when the non-detergent cosmetic composition is free of silicones, then the process according to the invention makes it possible to condition hair uniformly, thus giving it a pleasant feel, while at the same time controlling the volume and respecting the natural appearance of the head of hair, irrespective of the humidity to which the hair is subjected.

It has also been found that when the non-detergent cosmetic composition comprises one or more silicones, then the process according to the invention can give the head of hair an improved level of care and an improved appearance, the hair conserving its natural lightness.

The non-detergent compositions used in the process according to the invention have good working properties, i.e. these compositions can flow and be readily distributed over the entire head of hair. In addition, these compositions can be rinsed out easily.

One subject of the present invention is thus especially a cosmetic process for treating keratin fibres, in particular human keratin fibres such as the hair, in which:

a) a non-detergent cosmetic composition comprising, in a cosmetically acceptable medium, an amount of greater than or equal to 1% by weight, relative to the total weight of the composition, of one or more water-soluble inorganic calcium salts is applied to the said fibres, and then b) the said composition is rinsed out after an optional leave-in time.

Other subjects, characteristics, aspects and advantages of the invention will emerge even more clearly on reading the description and the examples that follow.

Calcium Salts

The non-detergent composition according to the invention comprises an amount of greater than or equal to 1% by weight, relative to the total weight of the composition, of one or more inorganic calcium salts.

The term "water-soluble calcium salt" means a calcium salt with a solubility in water at 20° C. of greater than or equal to 20 g/liter (g/L) of water, preferentially 100 g/L and even more preferentially 300 g/L.

Preferably, the inorganic calcium salts according to the invention have solubilities ranging from 30 to 4500 g/L.

The water-soluble calcium salts according to the invention are preferably chosen from inorganic calcium salts.

The calcium salts may be anhydrous or hydrated.

More particularly, the inorganic calcium salts used in the non-detergent composition according to the invention are chosen from calcium iodide, calcium bromide, calcium thiosulfate, calcium nitrate and calcium chloride, and mixtures thereof.

Even more preferentially, the inorganic calcium salt used in the non-detergent composition according to the invention is calcium chloride, especially calcium chloride dihydrate.

The inorganic calcium salt(s) used in the non-detergent composition according to the present invention are preferably present in the composition according to the invention in an amount ranging from 1% to 50% by weight, preferentially in an amount ranging from 1% to 20% by weight and even more preferentially in an amount ranging from 2% to 10% by weight relative to the total weight of the composition.

Silicones

The non-detergent cosmetic composition used in the treatment process according to the invention may comprise one or more silicones.

The silicone(s) that may be present in the non-detergent composition applied according to the invention are in particular polyorganosiloxanes that may be in the form of aqueous solutions, i.e. dissolved, or optionally in the form of dispersions or microdispersions, or of aqueous emulsions. The polyorganosiloxanes may also be in the form of oils, waxes, resins or gums.

Organopolysiloxanes are defined in greater detail in Walter Noll's *Chemistry and Technology of Silicones* (1968), Academic Press.

The silicone(s) may be volatile or non-volatile.

When they are volatile, the silicones are more particularly chosen from those with a boiling point of between 60° C. and 260° C., and even more particularly from:

(i) cyclic silicones comprising from 3 to 7 and preferably 4 to 5 silicon atoms.

These are, for example, octamethylcyclotetrasiloxane sold especially under the name Volatile Silicone 7207 by Union Carbide or Silbione 70045 V 2 by Rhône-Poulenc, decamethylcyclopentasiloxane sold under the name Volatile Silicone 7158 by Union Carbide, and Silbione 70045 V 5 by Rhône-Poulenc, and mixtures thereof.

Mention may also be made of cyclocopolymers of the dimethylsiloxane/methylalkylsiloxane type, such as Volatile Silicone FZ 3109 sold by the company Union Carbide, of chemical structure:

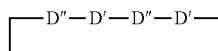

with D":

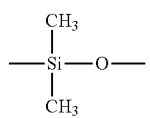

with D':

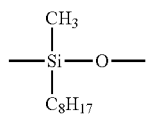

Mention may also be made of mixtures of cyclic silicones with organosilicon compounds, such as the mixture of octamethylcyclotetrasiloxane and tetrakis(trimethylsilyl)pentaerythritol (50/50) and the mixture of octamethylcyclotetrasiloxane and oxy-1,1'-bis(2,2,2',2',3,3'-hexatrimethylsilyloxy)neopentane;

(ii) linear volatile silicones containing 2 to 9 silicon atoms and having a viscosity of less than or equal to $5 \times 10^{-6}$ m²/s at 25° C. An example is decamethyltetrasiloxane sold especially under the name SH 200 by the company Toray Silicone. Silicones belonging to this category are also described in the article published in Cosmetics and Toiletries, Vol. 91, Jan. 76, pp. 27-32, Todd & Byers *Volatile Silicone Fluids for Cosmetics*.

Non-volatile silicones and more particularly polyalkylsiloxanes, polyarylsiloxanes, polyalkylarylsiloxanes, silicone gums and resins, and polyorganosiloxanes modified with organofunctional groups, and mixtures thereof, are preferably used.

These silicones are more particularly chosen from polyalkylsiloxanes, among which mention may be made mainly of polydimethylsiloxanes containing trimethylsilyl end groups (Dimethicone according to the CTFA name) having a viscosity of from $5 \times 10^{-6}$ to 2.5 m²/s at 25° C. and preferably $1 \times 10^{-5}$ to 1 m²/s. The viscosity of the silicones is measured, for example, at 25° C. according to standard ASTM 445 Appendix C.

Among these polyalkylsiloxanes, mention may be made, in a non-limiting manner, of the following commercial products:

the Silbione oils of the 47 and 70 047 series or the Mirasil oils sold by Rhône-Poulenc, for instance the oil 70047 V 500000;

the oils of the Mirasil series sold by the company Rhône-Poulenc;

the oils of the 200 series from the company Dow Corning, such as, more particularly, DC200 with a viscosity of 60000 cSt (centistokes);

the Viscasil oils from General Electric and certain oils of the SF series (SF 96, SF 18) from General Electric.

Mention may also be made of polydimethylsiloxanes containing dimethylsilanol end groups (Dimethiconol according to the CTFA name) such as the oils of the 48 series from the company Rhône-Poulenc.

Mention may also be made of polydimethylsiloxanes containing aminoethyl aminopropyl and α,ω-silanol groups.

In this category of polyalkylsiloxanes, mention may also be made of the products sold under the names Abil Wax 9800 and 9801 by the company Goldschmidt, which are poly($C_1$-$C_{20}$)alkylsiloxanes.

The polyalkylarylsiloxanes are particularly chosen from linear and/or branched polydimethylmethylphenylsiloxanes and polydimethyldiphenylsiloxanes with a viscosity of from $1 \times 10^{-5}$ to $5 \times 10^{-2}$ m$^2$/s at 25° C.

Among these polyalkylarylsiloxanes, examples that may be mentioned include the products sold under the following names:
- the Silbione oils of the 70 641 series from Rhône-Poulenc;
- the oils of the Rhodorsil 70 633 and 763 series from Rhône-Poulenc;
- the oil Dow Corning 556 Cosmetic Grade Fluid from Dow Corning;
- silicones of the PK series from Bayer, such as the product PK20;
- the silicones of the PN and PH series from Bayer, such as the products PN1000 and PH1000;
- certain oils of the SF series from General Electric, such as SF 1023, SF 1154, SF 1250 and SF 1265.

The silicone gums that may be present in the non-detergent composition according to the invention are especially polydiorganosiloxanes having high number-average molecular masses of between 200000 and 1000000, used alone or as a mixture in a solvent. This solvent can be chosen from volatile silicones, polydimethylsiloxane (PDMS) oils, polyphenylmethylsiloxane (PPMS) oils, isoparaffins, polyisobutylenes, methylene chloride, pentane, dodecane and tridecane, or mixtures thereof.

Mention may be made more particularly of the following products:
- polydimethylsiloxane gums,
- polydimethylsiloxane/methylvinylsiloxane gums,
- poly[(dimethylsiloxane)/(vinylhydrogenosiloxane)] gums,
- poly[(dimethylsiloxane)/(divinylhydrogenosiloxane)] gums,
- polydimethylsiloxane/diphenylsiloxane gums,
- polydimethylsiloxane/phenylmethylsiloxane gums,
- polydimethylsiloxane/diphenylsiloxane/methylvinylsiloxane gums.

Products that may be used more particularly are the following mixtures:
- mixtures formed from a polydimethylsiloxane hydroxylated at the end of the chain (known as dimethiconol according to the nomenclature of the CTFA dictionary) and from a cyclic polydimethylsiloxane (known as cyclomethicone according to the nomenclature of the CTFA dictionary), such as the product Q2 1401 sold by the company Dow Corning;
- mixtures formed from a polydimethylsiloxane gum with a cyclic silicone, such as the product SF 1214 Silicone Fluid from the company General Electric, this product being an SF 30 gum corresponding to a dimethicone, having a number-average molecular weight of 500 000, dissolved in the oil SF 1202 Silicone Fluid corresponding to decamethylcyclopentasiloxane;
- mixtures of two PDMSs with different viscosities, and more particularly of a PDMS gum and a PDMS oil, such as the product SF 1236 from the company General Electric. The product SF 1236 is a mixture of a gum SE 30 defined above with a viscosity of 20 m$^2$/s and of an oil SF 96 with a viscosity of $5 \times 10^{-6}$ m$^2$/s. This product preferably comprises 15% of gum SE 30 and 85% of an oil SF 96.

The organopolysiloxane resins that may be present in the composition according to the invention are crosslinked siloxane systems containing the following units: $R_2SiO_{2/2}$, $R_3SiO_{1/2}$, $RSiO_{3/2}$ and $SiO_{4/2}$ in which R represents a hydrocarbon group containing 1 to 16 carbon atoms or a phenyl group. Among these products, those that are particularly preferred are the ones in which R denotes a $C_1$-$C_4$ lower alkyl radical, more particularly methyl, or a phenyl radical.

Among these resins, mention may be made of the product sold under the name Dow Corning 593 or those sold under the names Silicone Fluid SS 4230 and SS 4267 by the company General Electric, which are silicones of dimethyl/trimethylsiloxane structure.

Mention may also be made of the trimethyl siloxysilicate type resins sold in particular under the names X22-4914, X21-5034 and X21-5037 by the company Shin-Etsu.

The organomodified silicones that may be present in the non-detergent composition according to the invention are silicones as defined above and comprising in their structure one or more organofunctional groups attached via a hydrocarbon-based radical.

Among the organomodified silicones, mention may be made of polyorganosiloxanes comprising:
- polyethyleneoxy and/or polypropyleneoxy groups optionally comprising $C_6$-$C_{24}$ alkyl groups, such as the oxyethylenated and oxypropylenated poly(methyllauryl/methylsiloxane) sold under the name Dow Corning 5200 Formulation Aid by the company Dow Corning (INCI: Lauryl PEG/PPG-18/18 methicone), the products known as dimethicone copolyol sold by the company Dow Corning under the name DC 1248 or the oils Silwet L 722, L 7500, L 77 and L 711 by the company Union Carbide, and the ($C_{12}$)alkylmethicone copolyol sold by the company Dow Corning under the name Q2 5200;
- thiol groups, such as the products sold under the names GP 72 A and GP 71 from Genesee;
- alkoxylated groups, such as the product sold under the name Silicone Copolymer F755 by SWS Silicones and Abil Wax 2428, 2434 and 2440 by the company Goldschmidt;
- hydroxylated groups, such as the polyorganosiloxanes containing a hydroxyalkyl function, described in French patent application FR-A-85/16334;
- acyloxyalkyl groups, for instance the polyorganosiloxanes described in U.S. Pat. No. 4,957,732;
- anionic groups of the phosphate or carboxylic acid type, for instance in the products described in patent EP 186 507 from the company Chisso Corporation, or of the alkylcarboxylic type, such as those present in the product X-22-3701E from the company Shin-Etsu; 2-hydroxyalkyl sulfonate; 2-hydroxyalkyl thiosulfate such as the products sold by the company Goldschmidt under the names Abil 5201 and Abil 5255;
- hydroxyacylamino groups, for instance the polyorganosiloxanes described in patent application EP 342 834. Mention may be made, for example, of the product Q2-8413 from the company Dow Corning.

Among the organomodified silicones, mention may also be made of amino silicones.

The term "amino silicone" means any polyaminosiloxane, i.e. any polysiloxane comprising at least one primary, secondary or tertiary amine function or a quaternary ammonium group.

Preferably, the amino silicone(s) used in the cosmetic composition according to the present invention are chosen from:
(a) the compounds corresponding to formula (I) below:

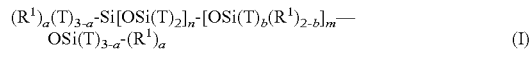

(I)

in which:

T is a hydrogen atom or a phenyl, hydroxyl (—OH) or $C_1$-$C_8$ alkyl radical, and preferably methyl, or a $C_1$-$C_8$ alkoxy, preferably methoxy, a denotes the number 0 or an integer from 1 to 3, and preferably 0, b denotes 0 or 1, and in particular 1, m and n are numbers such that the sum (n+m) can range especially from 1 to 2000 and in particular from 50 to 150, it being possible for n to denote a number from 0 to 1999 and in particular from 49 to 149, and for m to denote a number from 1 to 2000 and in particular from 1 to 10;

$R^1$ is a monovalent radical of formula —$C_qH_{2q}L$ in which q is a number from 2 to 8 and L is an optionally quaternized amino group chosen from the following groups:
—$N(R^2)$—$CH_2$—$CH_2$—$N(R^2)_2$;
—$N(R^2)_2$; —$N^+(R^2)_3Q^-$;
—$N^+(R^2)(H)_2Q^-$;
—$N^+(R^2)_2HQ^-$;
—$N(R^2)$—$CH_2$—$CH_2$—$N^+(R^2)(H)_2Q^-$, in which $R^2$ denotes a hydrogen atom, a phenyl, a benzyl or a saturated monovalent hydrocarbon-based radical, for example a $C_1$-$C_{20}$ alkyl radical, and $Q^-$ represents a halide ion, for instance fluoride, chloride, bromide or iodide.

In particular, the amino silicones corresponding to the definition of formula (I) are chosen from the compounds corresponding to formula (II) below:

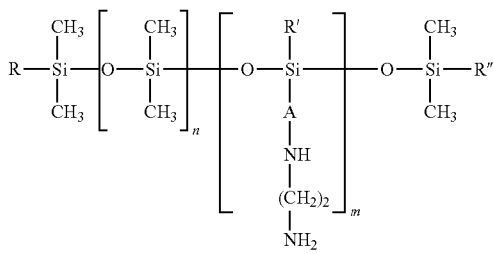

(II)

in which R, R' and R", which may be identical or different, denote a $C_1$-$C_4$ alkyl radical, preferably $CH_3$; a $C_1$-$C_4$ alkoxy radical, preferably methoxy; or OH; A represents a linear or branched, $C_3$-$C_8$ and preferably $C_3$-$C_6$ alkylene radical; m and n are integers dependent on the molecular weight and whose sum is between 1 and 2000.

According to a first possibility, R, R' and R", which may be identical or different, represent a $C_1$-$C_4$ alkyl or hydroxyl radical, A represents a $C_3$ alkylene radical and m and n are such that the weight-average molecular mass of the compound is between 5000 and 500000 approximately. Compounds of this type are referred to in the CTFA dictionary as "amodimethicones".

According to a second possibility, R, R' and R", which may be identical or different, represent a $C_1$-$C_4$ alkoxy or hydroxyl radical, at least one of the radicals R or R" is an alkoxy radical and A represents a $C_3$ alkylene radical. The hydroxy/alkoxy mole ratio is preferably between 0.2/1 and 0.4/1 and advantageously equal to 0.3/1. Moreover, m and n are such that the weight-average molecular mass of the compound is between 2000 and $10^6$. More particularly, n is between 0 and 999 and m is between 1 and 1000, the sum of n and m being between 1 and 1000.

In this category of compounds, mention may be made, inter alia, of the product Belsil® ADM 652 sold by Wacker.

According to a third possibility, R and R", which are different, represent a $C_1$-$C_4$ alkoxy or hydroxyl radical, at least one of the radicals R or R" is an alkoxy radical, R' represents a methyl radical and A represents a $C_3$ alkylene radical. The hydroxy/alkoxy mole ratio is preferably between 1/0.8 and 1/1.1 and advantageously equal to 1/0.95. Moreover, m and n are such that the weight-average molecular mass of the compound is between 2000 and 200000. More particularly, n is between 0 and 999 and m is between 1 and 1000, the sum of n and m being between 1 and 1000.

More particularly, mention may be made of the product Fluid WR® 1300 sold by Wacker.

According to a fourth possibility, R and R" represent a hydroxyl radical, R' represents a methyl radical and A is a $C_4$-$C_8$ and preferably $C_4$ alkylene radical. Moreover, m and n are such that the weight-average molecular mass of the compound is between 2000 and $10^6$. More particularly, n is between 0 and 1999 and m is between 1 and 2000, the sum of n and m being between 1 and 2000.

A product of this type is especially sold under the name DC 28299 by Dow Corning.

Note that the molecular mass of these silicones is determined by gel permeation chromatography (ambient temperature, polystyrene standard; µ styragem columns; eluent THF; flow rate 1 mm/m; 200 µl of a solution containing 0.5% by weight of silicone in THF are injected, and detection is performed by refractometry and UV-metry).

A product corresponding to the definition of formula (I) is in particular the polymer known in the CTFA dictionary (7$^{th}$ edition, 1997) as "trimethylsilyl amodimethicone", corresponding to formula (III) below:

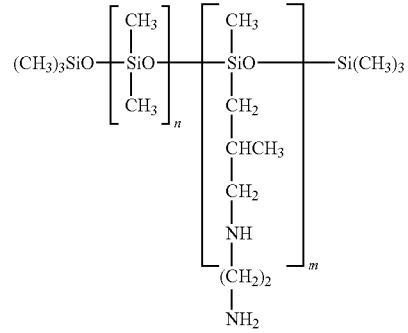

(III)

in which n and m have the meanings given above in accordance with formula (I) or (II).

Such compounds are described, for example, in patent application EP-A-0 095 238; a compound of formula (III) is sold, for example, under the name Q2-8220 by the company OSI.

(b) the compounds corresponding to formula (IV) below:

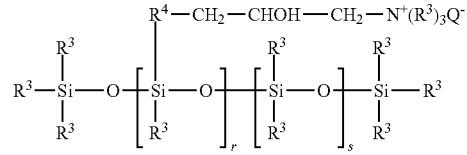

(IV)

in which:

R$^3$ represents a C$_1$-C$_{18}$ monovalent hydrocarbon-based radical, and in particular a C$_1$-C$_{18}$ alkyl or C$_2$-C$_{18}$ alkenyl radical, for example methyl;

R$^4$ represents a divalent hydrocarbon-based radical, especially a C$_1$-C$_{18}$ alkylene radical or a divalent C$_1$-C$_{18}$, and for example C$_1$-C$_8$, alkylenoxy radical;

Q$^-$ is a halide ion, in particular chloride;

r represents a mean statistical value from 2 to 20 and in particular from 2 to 8;

s represents a mean statistical value from 20 to 200 and in particular from 20 to 50.

Such compounds are described more particularly in U.S. Pat. No. 4,185,087.

A compound falling within this class is the product sold by the company Union Carbide under the name Ucar Silicone ALE 56.

(c) the quaternary ammonium silicones of formula (V):

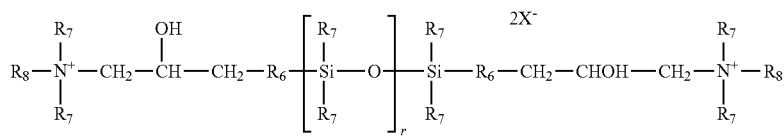
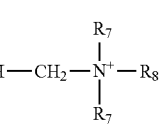

(V)

in which:

R$_7$, which may be identical or different, represent a monovalent hydrocarbon-based radical containing from 1 to 18 carbon atoms, and in particular a C$_1$-C$_{18}$ alkyl radical, a C$_2$-C$_{18}$ alkenyl radical or a ring comprising 5 or 6 carbon atoms, for example methyl;

R$_6$ represents a divalent hydrocarbon-based radical, especially a C$_1$-C$_{18}$ alkylene radical or a divalent C$_1$-C$_{18}$, and for example C$_1$-C$_8$, alkylenoxy radical linked to the Si via an SiC bond;

R$_8$, which may be identical or different, represent a hydrogen atom, a monovalent hydrocarbon-based radical containing from 1 to 18 carbon atoms, and in particular a C$_1$-C$_{18}$ alkyl radical, a C$_2$-C$_{18}$ alkenyl radical or a radical —R$_6$—NH-COR$_7$;

X$^-$ is an anion such as a halide ion, especially chloride, or an organic acid salt (acetate, etc.);

r represents a mean statistical value from 2 to 200 and in particular from 5 to 100;

These silicones are described, for example, in patent application EP-A 0 530 974.

d) the amino silicones of formula (VI) below:

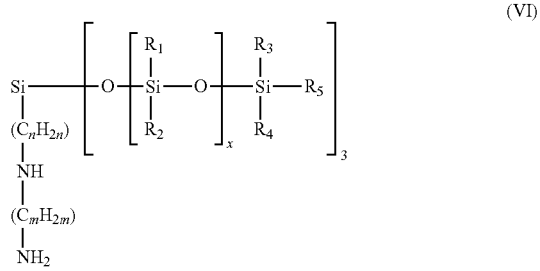

(VI)

in which:

R$_1$, R$_2$, R$_3$ and R$_4$, which may be identical or different, denote a C$_1$-C$_4$ alkyl radical or a phenyl group, R$_5$ denotes a C$_1$-C$_4$ alkyl radical or a hydroxyl group, n is an integer ranging from 1 to 5, m is an integer ranging from 1 to 5, and in which x is chosen such that the amine number is between 0.01 and 1 meq/g.

The silicone(s) that are particularly preferred are polysiloxanes containing amine groups such as the silicones of formula (II) or the silicones of formula (III).

When these compounds are used, one particularly advantageous embodiment involves their combined use with cationic and/or nonionic surfactants.

By way of example, it is possible to use the product sold under the name Cationic Emulsion DC 929 by the company Dow Corning, which comprises, besides amodimethicone, a cationic surfactant comprising a mixture of products corresponding to formula (VII):

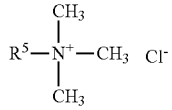

(VII)

in which R$^5$ denotes C$_{14}$-C$_{22}$ alkenyl and/or alkyl radicals derived from tallow fatty acids, and known under the CTFA name "tallowtrimonium chloride", in combination with a nonionic surfactant of formula:

C$_9$H$_{19}$—C$_6$H$_4$—(OC$_2$H$_4$)$_{10}$—OH, known under the CTFA name "Nonoxynol 10".

Use may also be made, for example, of the product sold under the name Cationic Emulsion DC 939 by the company Dow Corning, which comprises, besides amodimethicone, a cationic surfactant which is trimethylcetylammonium chloride and a nonionic surfactant of formula: C$_{13}$H$_{27}$—(OC$_2$H$_4$)$_{12}$—OH, known under the CTFA name "trideceth-12".

Another commercial product that may be used according to the invention is the product sold under the name Dow Corning Q2 7224 by the company Dow Corning, comprising, in combination, the trimethylsilyl amodimethicone of formula (C) described above, a nonionic surfactant of formula: C$_8$H$_{17}$—C$_6$H$_4$—(OCH$_2$CH$_2$)$_{40}$OH, known under the CTFA name "octoxynol-40", a second nonionic surfactant of formula: C$_{12}$H$_{25}$—(OCH$_2$—CH$_2$)$_6$—OH, known under the CTFA name "isolaureth-6", and propylene glycol.

Among all the silicones that may be present in the non-detergent composition applied according to the invention, it is preferred to choose the silicone(s) from among non-volatile silicones and more particularly polyalkylsiloxanes, polyarylsiloxanes, polyalkylarylsiloxanes, silicone gums, polyorganosiloxanes modified with organofunctional groups chosen from amino silicones, and silicones comprising polyethyleneoxy and/or polypropyleneoxy groups, and also mixtures thereof.

Preferably, the silicone(s) used in the non-detergent cosmetic composition applied according to the present invention are chosen from amino silicones.

The silicone(s) may be present in an amount ranging from 0.01% to 10% by weight, better still from 0.05% to 5% by weight and even better still from 0.1% to 2% by weight, relative to the total weight of the composition.

According to one embodiment, the non-detergent cosmetic composition applied according to the invention is free of silicone.

Fatty Substances

The non-detergent cosmetic composition used in the process according to the invention may also comprise one or more non-silicone fatty substances.

The term "fatty substance" means an organic compound that is insoluble in water at ordinary room temperature (25° C.) and at atmospheric pressure (760 mmHg), with a solubility in water of less than 5%, preferably 1% and even more preferentially 0.1%. In addition, fatty substances are generally soluble in organic solvents under the same temperature and pressure conditions, for instance chloroform, ethanol, benzene or liquid petroleum jelly.

Preferably, the non-silicone fatty substance(s) are chosen from fatty alcohols, fatty acids, esters of fatty acids and/or of fatty alcohols other than triglycerides, and non-silicone animal, plant, mineral or synthetic oils other than the abovementioned esters, and mixtures thereof.

a. Fatty Alcohols

For the purposes of the present invention, the term "fatty alcohol" means any saturated or unsaturated, linear or branched alcohol containing at least 8 carbon atoms.

The fatty alcohol may have the structure R—OH in which R denotes a saturated or unsaturated, linear or branched radical containing from 8 to 40 and preferably from 8 to 30 carbon atoms; R preferably denotes a $C_8$-$C_{40}$ and preferably $C_{12}$-$C_{24}$ alkyl or a $C_8$-$C_{40}$ and preferably $C_{12}$-$C_{24}$ alkenyl group. R may be substituted with one or more hydroxyl groups and especially with one or two hydroxyl groups.

Examples that may be mentioned include lauryl alcohol, cetyl alcohol, stearyl alcohol, oleyl alcohol, behenyl alcohol, linoleyl alcohol, undecylenyl alcohol, palmitoleyl alcohol, arachidonyl alcohol and erucyl alcohol, and mixtures thereof.

The fatty alcohol may represent a mixture of fatty alcohols, which means that several species of fatty alcohol may coexist, in the form of a mixture, in a commercial product.

Advantageously, the fatty alcohol is solid or pasty at a temperature of 25° C. For the purposes of the present invention, the term "fatty alcohol that is solid or pasty at 25° C." means a fatty alcohol that has a viscosity, measured with a rheometer (for example an R600 rheometer) at a shear rate of $1\ s^{-1}$, of greater than or equal to 1 Pa·s.

Preferably, the fatty alcohols used in the non-detergent cosmetic composition according to the invention are cetylstearyl alcohol, stearyl alcohol and cetyl alcohol.

b. Oils

As non-silicone oils that may be used in the non-detergent composition applied according to the invention, examples that may be mentioned include:

hydrocarbon-based oils of animal origin, such as perhydrosqualene;

triglycerides of plant or synthetic origin, such as liquid fatty acid triglycerides containing from 6 to 30 carbon atoms, for instance heptanoic or octanoic acid triglycerides, or alternatively, for example, sunflower oil, corn oil, soybean oil, marrow oil, grapeseed oil, sesame seed oil, hazelnut oil, apricot oil, macadamia oil, arara oil, castor oil, avocado oil, caprylic/capric acid triglycerides, for instance those sold by the company Stéarineries Dubois or those sold under the names Miglyol® 810, 812 and 818 by the company Dynamit Nobel, jojoba oil and shea butter oil;

linear or branched hydrocarbons of mineral or synthetic origin, containing more than 16 carbon atoms, such as volatile or non-volatile liquid paraffins, and derivatives thereof, petroleum jelly, liquid petroleum jelly, polydecenes, and hydrogenated polyisobutene such as Parleam®;

partially hydrocarbon-based fluoro oils; fluoro oils that may also be mentioned include perfluoromethylcyclopentane and perfluoro-1,3-dimethylcyclohexane, sold under the names Flutec® PC1 and Flutec® PC3 by the company BNFL Fluorochemicals; perfluoro-1,2-dimethylcyclobutane; perfluoroalkanes such as dodecafluoropentane and tetradecafluorohexane, sold under the names PF 5050® and PF 5060® by the company 3M, or bromoperfluorooctyl sold under the name Foralkyl® by the company Atochem; nonafluoromethoxybutane and nonafluoroethoxyisobutane; perfluoromorpholine derivatives such as 4-trifluoromethyl perfluoromorpholine sold under the name PF 5052® by the company 3M.

c. Esters

It is recalled that, for the purposes of the invention, the fatty esters and fatty acids more particularly contain one or more linear or branched, saturated or unsaturated hydrocarbon-based groups comprising from 1 to 30 and preferably 6 to 30 carbon atoms, which are optionally substituted, in particular with one or more hydroxyl groups (in particular 1 to 4). If they are unsaturated, these compounds may have one to three conjugated or unconjugated carbon-carbon double bonds.

Among the monoesters, mention may be made of dihydroabietyl behenate; octyldodecyl behenate; isocetyl behenate; cetyl lactate; $C_{12}$-$C_{15}$ alkyl lactate; isostearyl lactate; lauryl lactate; linoleyl lactate; oleyl lactate; (iso)stearyl octanoate; isocetyl octanoate; octyl octanoate; cetyl octanoate; decyl oleate; isocetyl isostearate; isocetyl laurate; isocetyl stearate; isodecyl octanoate; isodecyl oleate; isononyl isononanoate; isostearyl palmitate; methylacetyl ricinoleate; myristyl stearate; octyl isononanoate; 2-ethylhexyl isononate; octyl palmitate; octyl pelargonate; octyl stearate; octyldodecyl erucate; oleyl erucate; ethyl and isopropyl palmitates, 2-ethylhexyl palmitate, 2-octyldecyl palmitate, alkyl myristates such as isopropyl, butyl, cetyl, 2-octyldodecyl, myristyl or stearyl myristate, hexyl stearate, butyl stearate, isobutyl stearate; dioctyl malate, hexyl laurate, 2-hexyldecyl laurate.

Still within the context of this variant, esters of $C_4$-$C_{22}$ dicarboxylic or tricarboxylic acids and of $C_1$-$C_{22}$ alcohols and esters of monocarboxylic, dicarboxylic or tricarboxylic acids and of $C_2$-$C_{26}$ dihydroxy, trihydroxy, tetrahydroxy or pentahydroxy alcohols may also be used.

Mention may be made especially of: diethyl sebacate; diisopropyl sebacate; diisopropyl adipate; di-n-propyl adipate; dioctyl adipate; diisostearyl adipate; dioctyl maleate; glyceryl undecylenate; octyldodecyl stearoyl stearate; pentaerythrityl monoricinoleate; pentaerythrityl tetrasononanoate; pentaerythrityl tetrapelargonate; pentaerythrityl tetraisostearate; pentaerythrityl tetraoctanoate; propylene glycol dicaprylate; propylene glycol dicaprate; tridecyl erucate; triisopropyl citrate; triisostearyl citrate; glyceryl trilactate; glyceryl trioctanoate; trioctyldodecyl citrate; trioleyl citrate; propylene glycol dioctanoate; neopentyl glycol diheptanoate; diethylene glycol diisononanoate; and polyethylene glycol distearates.

Among the esters mentioned above, it is preferred to use ethyl, isopropyl, myristyl, cetyl or stearyl palmitate, 2-ethylhexyl palmitate, 2-octyldecyl palmitate, alkyl myristates such as isopropyl, butyl, cetyl or 2-octyldodecyl myristate, hexyl stearate, butyl stearate, isobutyl stearate; dioctyl malate, hexyl laurate, 2-hexyldecyl laurate, isononyl isononanoate or cetyl octanoate.

The composition may also comprise, as fatty ester, sugar esters and diesters of $C_6$-$C_{30}$, and preferably $C_{12}$-$C_{22}$ fatty acids. It is recalled that the term "sugar" means oxygen-bearing hydrocarbon-based compounds containing several alcohol functions, with or without aldehyde or ketone functions, and which comprise at least 4 carbon atoms. These sugars may be monosaccharides, oligosaccharides or polysaccharides.

Examples of suitable sugars that may be mentioned include sucrose (or saccharose), glucose, galactose, ribose, fucose, maltose, fructose, mannose, arabinose, xylose and lactose, and derivatives thereof, especially alkyl derivatives, such as methyl derivatives, for instance methylglucose.

The sugar esters of fatty acids may be chosen especially from the group comprising the esters or mixtures of esters of sugars described previously and of linear or branched, saturated or unsaturated $C_6$-$C_{30}$, and preferably $C_{12}$-$C_{22}$ fatty acids. If they are unsaturated, these compounds may have one to three conjugated or unconjugated carbon-carbon double bonds.

The esters according to this variant may also be selected from monoesters, diesters, triesters, tetraesters and polyesters, and mixtures thereof.

These esters may be, for example, oleates, laurates, palmitates, myristates, behenates, cocoates, stearates, linoleates, linolenates, caprates and arachidonates, or mixtures thereof such as, especially, oleopalmitate, oleostearate and palmitostearate mixed esters.

More particularly, use is made of monoesters and diesters and especially sucrose, glucose or methylglucose monooleates or dioleates, stearates, behenates, oleopalmitates, linoleates, linolenates and oleostearates.

An example that may be mentioned is the product sold under the name Glucate® DO by the company Amerchol, which is a methylglucose dioleate.

Examples of esters or mixtures of esters of sugar and of fatty acid that may also be mentioned include:
the products sold under the names F160, F140, F110, F90, F70 and SL40 by the company Crodesta, respectively denoting sucrose palmitostearates formed from 73% monoester and 27% diester and triester, from 61% monoester and 39% diester, triester and tetraester, from 52% monoester and 48% diester, triester and tetraester, from 45% monoester and 55% diester, triester and tetraester, from 39% monoester and 61% diester, triester and tetraester, and sucrose monolaurate;
the products sold under the name Ryoto Sugar Esters, for example referenced B370 and corresponding to sucrose behenate formed from 20% monoester and 80% di-tri-ester-polyester;
the sucrose mono-dipalmito-stearate sold by the company Goldschmidt under the name Tegosoft® PSE.

d. Fatty Acids

The fatty acids may be chosen from the acids of formula RCOOH, in which R is a saturated or unsaturated, linear or branched radical preferably comprising from 7 to 39 carbon atoms.

Preferably, R is a $C_7$-$C_{29}$ alkyl or $C_7$-$C_{29}$ alkenyl group and better still a $C_{12}$-$C_{24}$ alkyl or $C_{12}$-$C_{24}$ alkenyl group. R may be substituted with one or more hydroxyl groups and/or one or more carboxyl groups.

The fatty acid may be chosen in particular from lauric acid, oleic acid, palmitic acid, linoleic acid, myristic acid and stearic acid.

In order to be considered as a fatty acid, the fatty acid must not be in soap form, i.e. it must not be salified.

Preferably, the non-silicone fatty substance(s) are chosen from fatty alcohols and/or fatty acid esters.

The non-silicone solid fatty substance(s) are optionally present in the composition in an amount ranging from 0.1% to 30%, preferably in an amount ranging from 0.2% to 20%, and more preferably still in an amount ranging from 0.5% to 10% by weight, relative to the total weight of the composition.

Surfactants

The cosmetic composition according to the invention may also comprise one or more surfactants selected from cationic, anionic, nonionic, amphoteric and zwitterionic surfactants.

For the purposes of the present invention, the term "cationic surfactant" means a surfactant that is positively charged when it is contained in the composition according to the invention. This surfactant may bear one or more positive permanent charges or may contain one or more cationizable functions in the composition according to the invention.

As examples of cationic surfactants that may be used in the cosmetic composition, mention may be made especially of optionally polyoxyalkylenated primary, secondary or tertiary fatty amines, or salts thereof, and quaternary ammonium salts, and mixtures thereof.

The fatty amines generally comprise at least one $C_8$-$C_{30}$ hydrocarbon-based chain. Among the fatty amines that may be used according to the invention, an example that may be mentioned is stearylamidopropyldimethylamine.

Examples of quaternary ammonium salts that may especially be mentioned include:
those that have the general formula (VIII) below:

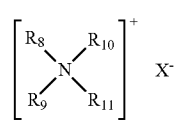

(VIII)

in which the radicals $R_8$ to $R_{11}$, which may be identical or different, represent a linear or branched aliphatic radical comprising from 1 to 30 carbon atoms or an aromatic radical such as aryl or alkylaryl, at least one of the radicals $R_8$ to $R_{11}$ comprising from 8 to 30 carbon atoms and preferably from 12 to 24 carbon atoms. The aliphatic radicals may comprise heteroatoms especially such as oxygen, nitrogen, sulfur and halogens.

The aliphatic radicals are, for example, chosen from alkyl, alkoxy, polyoxy($C_2$-$C_6$)alkylene, alkylamide, ($C_{12}$-$C_{22}$)alkylamido($C_2$-$C_6$)alkyl, ($C_{12}$-$C_{22}$)alkyl acetate or hydroxyalkyl radicals comprising approximately from 1 to 30 carbon atoms; $X^-$ is an anion chosen from the group of the halides, phosphates, acetates, lactates, ($C_2$-$C_6$)alkyl sulfates, or alkyl- or alkylaryl-sulfonates;

quaternary ammonium salts of imidazoline, such as, for example, those of formula (IX) below:

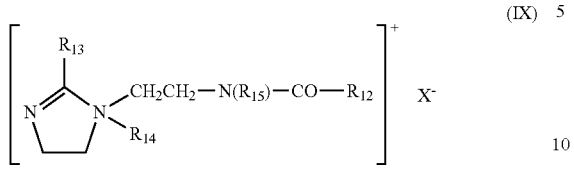

in which $R_{12}$ represents an alkenyl or alkyl radical comprising from 8 to 30 carbon atoms, for example derived from tallow fatty acids, $R_{13}$ represents a hydrogen atom, a $C_1$-$C_4$ alkyl radical or an alkenyl or alkyl radical comprising from 8 to 30 carbon atoms, $R_{14}$ represents a $C_1$-$C_4$ alkyl radical, $R_{15}$ represents a hydrogen atom or a $C_1$-$C_4$ alkyl radical and $X^-$ is an anion chosen from the group of halides, phosphates, acetates, lactates, alkyl sulfates, or alkyl- or alkylaryl-sulfonates. Preferably, $R_{12}$ and $R_{13}$ denote a mixture of alkenyl or alkyl radicals comprising from 12 to 21 carbon atoms, for example fatty acid derivatives of tallow, $R_{14}$ denotes a methyl radical and $R_{15}$ denotes a hydrogen atom. Such a product is sold, for example, under the name Rewoquat® W 75 by the company Rewo;

di- or triquaternary ammonium salts, in particular of formula (X):

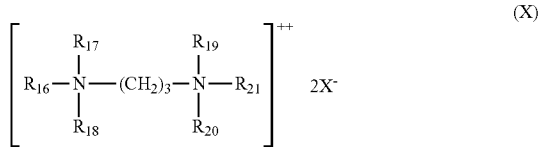

in which $R_{16}$ denotes an alkyl radical containing approximately from 16 to 30 carbon atoms, which is optionally hydroxylated and/or interrupted with one or more oxygen atoms and optionally branched, $R_{17}$ is selected from an alkyl radical containing from 1 to 4 carbon atoms or a group $(R_{16a})(R_{17a})(R_{18a})N^+$—$(CH_2)_3$—, $R_{16a}$, $R_{17a}$, $R_{18a}$, $R_{18}$, $R_{19}$, $R_{20}$ and $R_{21}$, which may be identical or different, are selected from hydrogen and an alkyl radical containing from 1 to 4 carbon atoms, and $X^-$ is an anion selected from the group of halides, acetates, phosphates, nitrates and methyl sulfates. Such compounds are, for example, Finquat CT-P, available from the company Finetex (Quaternium 89), and Finquat CT, available from the company Finetex (Quaternium 75), quaternary ammonium salts containing at least one ester function, such as those of formula (XI) below:

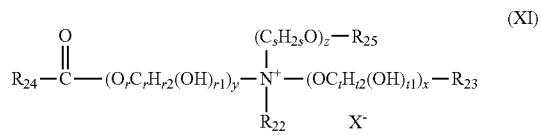

in which:

$R_{22}$ is chosen from $C_1$-$C_6$ alkyl radicals and $C_1$-$C_6$ hydroxyalkyl or dihydroxyalkyl radicals;

$R_{23}$ is chosen from:
the radical

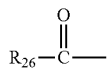

radicals $R_{27}$, which are linear or branched, saturated or unsaturated $C_1$-$C_{22}$ hydrocarbon-based radicals,
a hydrogen atom,
$R_{25}$ is chosen from:
the radical

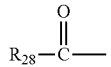

radicals $R_{29}$, which are linear or branched, saturated or unsaturated $C_1$-$C_6$ hydrocarbon-based radicals,
a hydrogen atom,
$R_{24}$, $R_{26}$ and $R_{28}$, which may be identical or different, are chosen from linear or branched, saturated or unsaturated $C_7$-$C_{21}$ hydrocarbon-based radicals;
r, s and t, which may be identical or different, are integers ranging from 2 to 6;
y is an integer ranging from 1 to 10;
x and z, which may be identical or different, are integers ranging from 0 to 10;
$r_1$ or $t_1$=0 or 1,
$r_2+r_1=2r$,
$t_2+t_1=2t$,
$X^-$ is a simple or complex, organic or mineral anion;
with the proviso that the sum x+y+z is from 1 to 15, that when x is 0, then $R_{23}$ denotes $R_{27}$ and that when z is 0, then $R_{25}$ denotes $R_{29}$.

The alkyl radicals $R_{22}$ may be linear or branched, but more particularly linear.

$R_{22}$ preferably denotes a methyl, ethyl, hydroxyethyl or dihydroxypropyl radical, and more particularly a methyl or ethyl radical.

Advantageously, the sum x+y+z is from 1 to 10.

When $R_{23}$ is a hydrocarbon-based radical $R_{27}$, it may be long and may contain from 12 to 22 carbon atoms, or may be short and may contain from 1 to 3 carbon atoms.

When $R_{25}$ is a hydrocarbon-based radical $R_{29}$, it preferably contains 1 to 3 carbon atoms.

Advantageously, $R_{24}$, $R_{26}$ and $R_{28}$, which may be identical or different, are chosen from linear or branched, saturated or unsaturated $C_{11}$-$C_{21}$ hydrocarbon-based radicals, and more particularly from linear or branched, saturated or unsaturated $C_{11}$-$C_{21}$ alkyl and alkenyl radicals.

Preferably, x and z, which may be identical or different, are equal to 0 or 1.

Advantageously, y is equal to 1.

Preferably, r, s and t, which may be identical or different, are equal to 2 or 3, and even more particularly are equal to 2.

The anion $X^-$ is preferably a halide (chloride, bromide or iodide) or an alkyl sulfate, more particularly methyl sulfate. It is possible, however, to use methanesulfonate, phosphate, nitrate or tosylate, an anion derived from organic acid, such as acetate or lactate, or any other anion that is compatible with ester-functional ammonium.

The anion $X^-$ is even more particularly chloride or methyl sulfate.

Use is made more particularly in the composition according to the invention of the ammonium salts of formula (XI) in which:

$R_{22}$ denotes a methyl or ethyl radical,
x and y are equal to 1;
z is equal to 0 or 1;
r, s and t are equal to 2;
$R_{23}$ is chosen from:
the radical

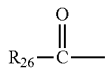

methyl, ethyl or $C_{14}$-$C_{22}$ hydrocarbon-based radicals,
a hydrogen atom;
$R_{25}$ is chosen from:
the radical

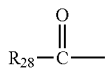

a hydrogen atom;
$R_{24}$, $R_{26}$ and $R_{28}$, which may be identical or different, are chosen from linear or branched, saturated or unsaturated $C_{13}$-$C_{17}$ hydrocarbon-based radicals and preferably from linear or branched, saturated or unsaturated $C_{13}$-$C_{17}$ alkyl and alkenyl radicals.

The hydrocarbon-based radicals are advantageously linear.

Mention may be made, for example, of the compounds of formula (XI) such as diacyloxyethyldimethylammonium, diacyloxyethylhydroxyethylmethylammonium, monoacyloxyethyldihydroxyethylmethylammonium, triacyloxyethylmethylammonium or monoacyloxyethylhydroxyethyldimethylammonium salts (chloride or methyl sulfate, in particular), and mixtures thereof. The acyl radicals preferably contain 14 to 18 carbon atoms and are obtained more particularly from a plant oil such as palm oil or sunflower oil. When the compound contains several acyl radicals, these radicals may be identical or different.

These products are obtained, for example, by direct esterification of triethanolamine, triisopropanolamine, an alkyldiethanolamine or an alkyldiisopropanolamine, which are optionally oxyalkylenated, with fatty acids or with fatty acid mixtures of plant or animal origin, or by transesterification of the methyl esters thereof. This esterification is followed by a quaternization using an alkylating agent such as an alkyl halide (preferably a methyl or ethyl halide), a dialkyl sulfate (preferably dimethyl or diethyl sulfate), methyl methanesulfonate, methyl para-toluenesulfonate, glycol chlorohydrin or glycerol chlorohydrin.

Such compounds are, for example, sold under the names Dehyquart® by Henkel, Stepanquat® by Stepan, Noxamium® by Ceca or Rewoquat® WE 18 by Rewo-Witco.

The composition according to the invention preferably contains a mixture of quaternary ammonium salts of mono-, di- and triesters with a weight majority of diester salts.

Examples of mixtures of ammonium salts that may be used include the mixture containing 15% to 30% by weight of acyloxyethyldihydroxyethylmethylammonium methyl sulfate, 45% to 60% of diacyloxyethylhydroxyethylmethylammonium methyl sulfate and 15% to 30% of triacyloxyethylmethylammonium methyl sulfate, the acyl radicals containing from 14 to 18 carbon atoms and being derived from palm oil that is optionally partially hydrogenated.

It is also possible to use the ammonium salts containing at least one ester function that are described in patents U.S. Pat. Nos. 4,874,554 and 4,137,180.

Preferably, the cosmetic composition according to the invention comprises one or more surfactants chosen from the compounds of formula (VIII) or (XI).

Preference is given, among the quaternary ammonium salts of formula (VIII), on the one hand, to tetraalkylammonium chlorides, such as, for example, dialkyldimethylammonium or alkyltrimethylammonium chlorides in which the alkyl radical comprises approximately from 12 to 22 carbon atoms, in particular behenyltrimethylammonium chloride, distearyldimethylammonium chloride, cetyltrimethylammonium chloride or benzyldimethylstearylammonium chloride, or also, on the other hand, to distearoylethylhydroxyethylmethylammonium methosulfate, dipalmitoylethylhydroxyethylammonium methosulfate or distearoylethylhydroxyethylammonium methosulfate, or also, finally, to palmitylamidopropyltrimethylammonium chloride or stearamidopropyldimethyl(myristyl acetate)ammonium chloride, sold under the name Ceraphyl® 70 by Van Dyk.

Among all the cationic surfactants that may be present in the composition according to the invention, cationic surfactants from among cetyltrimethylammonium (INCI: cetrimonium), behenyltrimethylammonium (INCI: behentrimonium), dipalmitoylethylhydroxyethylmethylammonium, distearoylethylhydroxyethylmethylammonium, methyl($C_9$-$C_{19}$) alkyl($C_{10}$-$C_{20}$)alkylamidoethylimidazolium and stearamidopropyldimethylamine salts (chloride or methosulfate), and the stearamidopropyldimethylammonium salt, and mixtures thereof, are preferably chosen.

Use may be made of behenoylhydroxypropyltrimethylammonium chloride sold by KAO under the name Quatarmin BTC 131.

When they are present, the amount of the cationic surfactant(s) preferably ranges from 0.01% to 20% by weight and better still from 0.1% to 5% by weight relative to the total weight of the composition.

The term "anionic surfactant" means a surfactant comprising, as ionic or ionizable groups, only anionic groups. These anionic groups are preferably chosen from $CO_2H$, $CO_2^-$, $SO_3H$, $SO_3^-$, $OSO_3H$, $OSO_3^-$, $H_2PO_3$, $HPO_3^-$, $PO_3^{2-}$, $H_2PO_2$, $HPO_2$, $HPO_2^-$, $PO_2^-$, $POH$ and $PO^-$ groups.

As examples of anionic surfactants that may be used in the composition according to the invention, mention may be made of alkyl sulfates, alkyl ether sulfates, alkylamido ether sulfates, alkylarylpolyether sulfates, monoglyceride sulfates, alkylsulfonates, alkylamidesulfonates, alkylarylsulfonates, α-olefin sulfonates, paraffin sulfonates, alkylsulfosuccinates, alkylether sulfosuccinates, alkylamide sulfosuccinates, alkylsulfoacetates, acylsarcosinates, acylglutamates, alkylsulfosuccinamates, acylisethionates and N-acyltaurates, salts of alkyl monoesters of polyglycoside-polycarboxylic acids, acyllactylates, D-galactoside uronic acid salts, alkyl ether carboxylic acid salts, alkylaryl ether carboxylic acid salts, alkylamido ether carboxylic acid salts; and the corresponding non-salified forms of all these compounds; the alkyl and acyl groups of all these compounds comprising from 6 to 24 carbon atoms and the aryl group denoting a phenyl group.

These compounds may be oxyethylenated and then preferably comprise from 1 to 50 ethylene oxide units.

The salts of $C_{6-24}$ alkyl monoesters of polyglycoside-polycarboxylic acids may be chosen from $C_{6-24}$ alkyl polyglycoside citrates, $C_{6-24}$ alkyl polyglycoside tartrates and $C_{6-24}$ alkyl polyglycoside sulfosuccinates.

When the anionic surfactant(s) (ii) are in salt form, they may be chosen from alkali metal salts such as the sodium or potassium salt and preferably the sodium salt, the ammonium salts, the amine salts and in particular amino alcohol salts or the alkaline-earth metal salts such as the magnesium salt.

Examples of amino alcohol salts that may especially be mentioned include monoethanolamine, diethanolamine and triethanolamine salts, monoisopropanolamine, diisopropanolamine or triisopropanolamine salts, 2-amino-2-methyl-1-propanol salts, 2-amino-2-methyl-1,3-propanediol salts and tris(hydroxymethyl)aminomethane salts.

Alkali metal or alkaline-earth metal salts and in particular the sodium or magnesium salts are preferably used.

Among the anionic surfactants, it is preferred, according to the invention, to use alkyl sulfate salts and alkyl ether sulfate salts and mixtures thereof.

When they are present, the amount of the anionic surfactant(s) is preferably within the range from 0.1% to 3.5% by weight, relative to the total weight of the composition.

Even more preferentially, the cosmetic composition used in the process according to the invention does not contain any anionic surfactants.

Examples of additional nonionic surfactants that may be used in the compositions of the present invention are described, for example, in the Handbook of Surfactants by M. R. Porter, published by Blackie & Son (Glasgow and London), 1991, pp. 116-178. They are especially chosen from polyethoxylated, polypropoxylated or polyglycerolated alcohols, α-diols and ($C_{1-20}$)alkylphenols, containing at least one fatty chain comprising, for example, from 8 to 18 carbon atoms, the number of ethylene oxide or propylene oxide groups possibly ranging especially from 2 to 50, and the number of glycerol groups possibly ranging especially from 2 to 30.

Mention may also be made of condensates of ethylene oxide and of propylene oxide with fatty alcohols; polyethoxylated fatty amides preferably having from 2 to 30 ethylene oxide units, polyglycerolated fatty amides containing on average 1 to 5, and in particular 1.5 to 4, ethoxy related fatty acid esters of sorbitan containing from 2 to 30 ethylene oxide units, fatty acid esters of sucrose, fatty acid esters of polyethylene glycol, ($C_{6-24}$ alkyl)polyglycosides, N—($C_{6-24}$ alkyl) glucamine derivatives, amine oxides such as ($C_{10}C_{14}$)alkylamine oxides or N($C_{10-14}$ acyl)aminopropylmorpholine oxides.

When they are present, the amount of the nonionic surfactant(s) is preferably within the range from 0.1% to 3.5% by weight, relative to the total weight of the composition.

The amphoteric or zwitterionic surfactant(s) that may be used in the present invention may especially be optionally quaternized, secondary or tertiary aliphatic amine derivatives, in which the aliphatic group is a linear or branched chain containing from 8 to 22 carbon atoms, the said amine derivatives containing at least one anionic group such as, for example, a carboxylate, sulfonate, sulfate, phosphate or phosphonate group. Mention may be made in particular of ($C_8$-$C_{20}$)alkylbetaines, sulfobetaines, ($C_8$-$C_{20}$) alkyl)amido($C_{3-8}$ alkyl)betaines and ($C_8$-$C_{20}$ alkyl)amido($C_6$-$C_8$ alkyl)sulfobetaines. Among the optionally quaternized secondary or tertiary aliphatic amine derivatives that can be used, as defined above, mention may also be made of the compounds of respective structures (A1) and (A2) below:

$$R_a\text{—CONHCH}_2\text{CH}_2\text{—N+}(R_b)(R_c)(\text{CH}_2\text{COO}^-) \quad (A1)$$

in which:
$R_a$ represents a $C_{10}$-$C_{30}$ alkyl or alkenyl group derived from an acid $R_a$—COOH preferably present in hydrolysed coconut oil, a heptyl group, a nonyl group or an undecyl group,
$R_b$ represents a β-hydroxyethyl group, and
$R^c$ represents a carboxymethyl group;
and $$R_a'\text{—CONHCH}_2\text{CH}_2\text{—N(B)(B')} \quad (A2)$$

in which:
B represents —CH$_2$CH$_2$OX',
B' represents —(CH$_2$)$_z$—Y', with z=1 or 2,
X' represents the group —CH$_2$—COOH, CH$_2$—COOZ', —CH$_2$CH$_2$—COOH, —CH$_2$CH$_2$—COOZ', or a hydrogen atom,
Y' represents —COOH, —COOZ', the group —CH$_2$—CHOH—SO$_3$H or —CH$_2$—CHOH—SO$_3$Z',
Z' represents an ion derived from an alkali metal or alkaline-earth metal, such as sodium, an ammonium ion or an ion derived from an organic amine.
Ra' represents a $C_{10}$-$C_{30}$ alkyl or alkenyl group of an acid Ra'—COOH which is preferably present in coconut oil or in hydrolysed linseed oil, or an alkyl group, especially a $C_{17}$ group, and its iso form, or an unsaturated $C_{17}$ group.

These compounds are classified in the CTFA dictionary, 5th edition, 1993, under the names disodium cocoamphodiacetate, disodium lauroamphodiacetate, disodium caprylamphodiacetate, disodium caprylamphodiacetate, disodium cocoamphodipropionate, disodium lauroamphodipropionate, disodium caprylamphodipropionate, disodium caryloamphodipropionate, lauroamphodipropionic acid and cocoamphodipropionic acid.

By way of example, mention may be made of the cocoamphodiacetate sold by the company Rhodia under the trade name Miranol® C2M Concentrate.

Among the amphoteric or zwitterionic surfactants mentioned above that are preferably used are ($C_{8-20}$ alkyl)betaines and ($C_{8-20}$ alkyl)amido($C_{6-8}$ alkyl)betaines such as cocamidopropylbetaine, and mixtures thereof.

When they are present, the amount of the amphoteric or zwitterionic surfactant(s) is preferably within the range from 0.1% to 3.5% by weight, relative to the total weight of the composition.

Preferably, the cosmetic composition comprises one or more cationic surfactants.

Even more preferentially, the cationic surfactant(s) that may be used in the cosmetic composition according to the invention are chosen from the compounds of formula (I) or (IV) and more particularly from cetyltrimethylammonium and behenyltrimethylammonium salts.

The non-detergent cosmetic composition used in the process according to the invention may comprise one or more thickeners other than the abovementioned fatty alcohols or fatty esters.

For the purposes of the present invention, the term "thickener" means any compound whose presence increases the viscosity of the composition into which it is introduced by at least 25 cps and preferably 50 cps at 25° C. and at a shear rate of 1 s$^{-1}$.

The thickener(s) may be chosen from fatty acid amides, oxyalkylenated fatty acid esters and thickening polymers, or mixtures thereof.

Preferably, the thickener(s) used in the non-detergent composition according to the invention are nonionic.

In particular, the thickeners used in the non-detergent composition according to the invention are chosen from non-associative nonionic thickening polymers.

Preferentially, the thickeners used in the non-detergent composition according to the invention are chosen from celluloses and more particularly from hydroxyethylcellulose and hydroxypropylcellulose.

Even more preferentially, the thickener used in the non-detergent composition according to the invention is hydroxyethylcellulose.

The thickener(s), which are preferably nonionic or cationic, used in the non-detergent composition according to the present invention may be present in the composition in an amount ranging from 0.01% to 10% by weight and even more preferentially in an amount ranging from 0.1% to 5% by weight, relative to the total weight of the composition.

The compositions of the invention comprise a cosmetically acceptable medium.

The term "cosmetically acceptable medium" means a medium that is compatible with keratin fibres, such as the hair.

The cosmetically acceptable medium is formed from water or from a mixture of water and one or more cosmetically acceptable solvents chosen from $C_1$-$C_4$ lower alcohols, such as ethanol, isopropanol, tert-butanol or n-butanol; polyols such as glycerol, propylene glycol and polyethylene glycols; and mixtures thereof.

The composition according to the invention may comprise an amount of water which is greater than or equal to 5% by weight, relative to the total weight of the composition, preferably an amount of water greater than or equal to 20% by weight relative to the total weight of the composition.

Preferably, the amount of water in the composition according to the invention is less than or equal to 95% and preferentially less than or equal to 90% by weight relative to the total weight of the composition. The organic solvents may be present in a concentration ranging from 0.1% to 40% and better still from 1% to 20% by weight relative to the total weight of the composition.

The pH of the compositions according to the invention generally ranges from 3 to 11.

The non-detergent composition according to the invention may also comprise one or more standard additives that are well known in the art, chosen from moisturizers; emollients, plasticizers, permanent or temporary dyes such as natural or synthetic direct dyes (base or coupler) or mixtures thereof, fragrances, peptizers, preserving agents, active agents, ceramides or pseudoceramides; vitamins or provitamins; pH stabilizers, preserving agents; proteins, sequestrants; solubilizers; reducing agents or antioxidants; oxidizing agents; basifying agents, acidifying agents, anticorrosion agents and cationic polymers, and mixtures thereof.

A person skilled in the art will take care to select the standard additives and the amount thereof such that they do not harm the properties of the non-detergent compositions of the present invention.

These standard additives are generally present in the composition according to the invention in an amount ranging from 0 to 20% by weight relative to the total weight of the composition.

The non-detergent composition according to the invention may be in the form of an emulsion. More specifically, it may be either in the form of an oil-in-water emulsion, with the continuous phase being the aqueous phase, or in the form of a water-in-oil emulsion, with the continuous phase being the fatty phase.

The non-detergent cosmetic compositions used in the process according to the invention may be hair conditioners.

The compositions described above may be used on any type of hair: light or dark hair, natural hair or hair that has undergone a cosmetic treatment such as permanent waving, dyeing, bleaching or relaxing.

The cosmetic composition according to the invention may be used on wet or dry hair. Preferably, the non-detergent cosmetic composition is applied to clean hair.

Moreover, the leave-on time of the non-detergent cosmetic composition on the hair may be between a few seconds and 30 minutes, preferably between 10 seconds and 15 minutes and even more preferentially between 1 minute and 10 minutes.

The application to the hair of the cosmetic composition according to the invention may be performed, for example, using a comb, a fine brush, a coarse brush or with the fingers.

The amount applied is an amount that is effective for producing an effect on the type of hair used. This amount may generally range from 0.01 to 1 g of composition per gram of hair, and preferably from 0.05 to 0.5 g.

Rinsing is preferably performed with water.

According to one particular embodiment of the invention, the rinsing of the non-detergent composition is followed by drying at room temperature or at a temperature above 40° C.

The drying may be performed immediately after the application or after a leave-on time that may range from 1 minute to 30 minutes.

Preferably, the hair is dried, in addition to using a supply of heat, with a flow of air. This flow of air during drying makes it possible to improve the individualization of the coating.

During drying, a mechanical action may be exerted on the locks, such as combing, brushing or running the fingers through the hair.

The drying step of the process of the invention may be performed with a hood, a hair dryer or a straightening iron.

When the drying step is performed with a hood or a hair dryer, the drying temperature is between 40 and 110° and preferably between 50 and 90°.

When the drying step is performed with a straightening iron, the drying temperature is between 110 and 220° and preferably between 130 and 200°.

The examples below are given as illustrations of the present invention.

EXAMPLES

The examples that follow are given as non-limiting illustrations of the present invention.

Example 1 a. Compositions

A non-detergent hair treatment composition 1 applied according to the invention is prepared from the ingredients indicated in the table below, the amounts of which are expressed as weight percentages of active material relative to the total weight of the composition.

|  | Composition 1 (invention) |
|---|---|
| Calcium chloride dihydrate | 4 |
| Water | qs 100% | b. Procedure

A panel of experts evaluates the cosmetic effects provided by a composition 1 according to the invention and a reference aqueous composition not containing calcium chloride.

Each comparison is performed on a panel of 20 women: 10 women with natural hair and 10 women with sensitized hair. The term "sensitized hair" means hair that has undergone prior chemical or physical treatments.

6 to 10 g of each of these compositions, as a function of the length of the hair, are applied to each half-head. After application, the hair is rinsed, combed and then dried by blow-drying or in the open air.

c. Evaluation of the Cosmetic Performance

| Criteria | | Locks treated with composition 1 according to the invention | Locks treated with an aqueous composition free of calcium chloride |
|---|---|---|---|
| Wet hair | Smoothness | +++ | – |
| | Suppleness | + | – |
| | Sensation of having finer hair | ++ | – |
| | Speed of drying | +++ | – |
| Hair dry | Smoothness | +++ | – |
| | Sheen | +++ | – |
| | Silky feel | +++ | – |
| | Sensation of having finer hair | ++ | – |
| | Lightness | +++ | – |

It is found that, on wet hair, hair treated with the non-detergent cosmetic composition 1 according to the invention is smoother, more supple and finer than hair treated with water. The hair dries more quickly.

Furthermore, it is observed that, on dry hair, hair treated with the cosmetic composition 1 according to the invention is smoother, shinier, lighter and finer and has a silkier feel than hair treated with water.

The panel of experts also observes that composition 1 according to the invention makes the hair feel appreciably lighter.

Example 2 a. Composition

A non-detergent composition (2) applied according to the invention is prepared, the amounts of which are expressed as weight percentages of active material relative to the total weight of the composition, unless otherwise indicated.

| | Composition 2 |
|---|---|
| Myristyl/cetyl/stearyl myristate/palmitate/stearate mixture (Crodamol MSPA from Croda) | 1 |
| Hydroxyethylcellulose (Natrosol 250 HHR from Aqualon) | 1 |
| Cetyltrimethylammonium chloride as an aqueous 25% solution (Dehyquart A OR from Cognis) | 0.6 |
| Calcium chloride dihydrate | 4 |
| Water | qs 100% | b. Procedure

On a panel of 20 women consisting of 10 women with natural hair and 10 women with sensitized hair, this composition leads to results similar to those obtained with composition A of Example 1.

Relative to a composition containing an amino silicone instead of the calcium salt, greater lightness and a faster drying speed are obtained with the composition according to the invention.

c. Evaluation of the Control of the Volume of the Hair

The study of the control of the volume is performed on locks of natural and sensitized hair (SA20), weighing 2.7 g each.

1 g of each of the compositions described in Examples 1 and 2 is applied to the wet locks. The locks are then rinsed and dried with a hairdryer, before being suspended in a glove box placed at 75% relative humidity.

The volume of the locks is then evaluated.

| Criterion | Locks treated with the aqueous composition | Locks treated with composition 1 according to the invention | Locks treated with composition 2 according to the invention |
|---|---|---|---|
| Absence of frizziness | + | ++++ | ++++ |

Observation of the volume of the locks at high humidity shows that compositions 1 and 2 according to the invention afford better control of the volume of the locks than the reference aqueous composition; in particular, a decrease in frizziness is observed.

A decrease in frizziness is also observed relative to a composition 2 in which the calcium salt has been replaced with an amino silicone.

This study is confirmed by tests on heads in a humid climate on 20 women, with natural to sensitized hair and with a degree of frizziness ranging from 1 to 3.

The expert and the consumers observe control of the volume of the head of hair at high relative humidity over a period of more than 24 hours.

Example 3

A non-detergent composition (3) applied according to the invention is prepared, the amounts of which are expressed as weight percentages of active material relative to the total weight of the composition, unless otherwise indicated.

| | Composition 3 |
|---|---|
| Myristyl/cetyl/stearyl myristate/palmitate/stearate mixture (Crodamol MSPA from Croda) | 1 |
| Hydroxyethylcellulose (Natrosol 250 HHR from Aqualon) | 1 |
| Cetyltrimethylammonium chloride as an aqueous 25% solution (Dehyquart A OR from Cognis) | 0.6 |
| Calcium chloride dihydrate | 8 |
| Water qs | 100% |

The invention claimed is:

1. A treatment process for treating keratin fibers, comprising:
   a) applying to the keratin fibers a non-detergent cosmetic composition comprising, in a cosmetically acceptable medium, an amount of greater than or equal to about 1% by weight, relative to the total weight of the composition, of at least one water-soluble inorganic calcium salt, and further comprising at least one fatty substance chosen from fatty alcohols; fatty acids; esters of fatty alcohols other than triglycerides; and non-silicone animal, plant, mineral and synthetic oils other than esters of fatty acids and esters of fatty alcohols other than triglycerides, and b) rinsing out the composition after a leave-in time.

2. The treatment process according to claim 1, wherein the keratin fibers are hair.

3. The treatment process according to claim 1, wherein the at least one water-soluble inorganic calcium salt is chosen from calcium iodide, calcium bromide, calcium thiosulfate, calcium nitrate, calcium chloride, and mixtures thereof.

4. The treatment process according to claim 1, wherein the at least one water-soluble inorganic calcium salt is calcium chloride.

5. The treatment process according to claim 1, wherein the amount of at least one water-soluble inorganic calcium salt ranges from about 1% to about 50% by weight, relative to the total weight of the composition.

6. The treatment process according to claim 5, wherein the amount of at least one water-soluble inorganic calcium salt ranges from about 2% to about 10% by weight, relative to the total weight of the composition.

7. The treatment process according to claim 1, wherein the non-detergent cosmetic composition further comprises at least one silicone.

8. The treatment process according to claim 7, wherein the at least one silicone is chosen from amino silicones.

9. The treatment process according to claim 1, wherein the at least one fatty substance is chosen from fatty alcohols and fatty acid esters.

10. The treatment process according to claim 1, wherein the non-detergent cosmetic composition further comprises at least one surfactant chosen from anionic, cationic, nonionic, zwitterionic and amphoteric surfactants.

11. The treatment process according to claim 10, wherein the at least one surfactant is chosen from cationic surfactants.

12. The treatment process according to claim 11, wherein the cationic surfactants are chosen from at least one of salts of optionally polyoxyalkylenated primary, secondary, and tertiary fatty amines, and quaternary ammonium salts.

13. The treatment process according to claim 11, wherein the cationic surfactants are chosen from at least one of cetyltrimethylammonium, behenyltrimethylammonium, dipalmitoylethylhydroxyethylmethylammonium, distearoylethylhydroxyethylmethylammonium, methyl($C_9$-$C_{19}$)alkyl($C_{10}$-$C_{20}$)alkylamidoethylimidazolium salts, stearamidopropyldimethylamine, and stearamidopropyldimethylammonium salts.

14. The treatment process according claim 1, wherein the non-detergent cosmetic composition further comprises at least one thickener chosen from nonionic and cationic thickeners.

15. The treatment process according to claim 14, wherein the nonionic thickeners are chosen from non-associative nonionic thickening polymers.

16. The treatment process according to claim 15, wherein the non-associative nonionic thickening polymers are polysaccharides.

17. The treatment process according claim 1, wherein the non-detergent cosmetic composition is free of anionic surfactants.

18. The treatment process according to claim 1, wherein the leave-on time of the composition ranges from less than about 10 seconds to about 30 minutes.

19. The treatment process according to claim 18, wherein the leave-on time of the composition ranges from about 1 minute to about 10 minutes.

* * * * *